(12) United States Patent
Hintermann (10) Patent No.: US 10,314,713 B2
(45) Date of Patent: Jun. 11, 2019

(54) ANKLE PROSTHESIS WITH NEUTRAL POSITION ADJUSTMENT

(71) Applicant: EUROPEAN FOOT PLATFORM SC, Saint Louis (FR)

(72) Inventor: Beat Hintermann, Liestal (CH)

(73) Assignee: EUROPEAN FOOT PLATFORM SC, Saint Louis (FR)

( * ) Notice: Subject to any disclaimer, the term of this patent is extended or adjusted under 35 U.S.C. 154(b) by 0 days.

(21) Appl. No.: 15/060,125

(22) Filed: Mar. 3, 2016

(65) Prior Publication Data

US 2016/0324650 A1    Nov. 10, 2016

Related U.S. Application Data

(63) Continuation of application No. 11/553,252, filed on Oct. 26, 2006, now Pat. No. 9,278,006.

(51) Int. Cl.
*A61F 2/42* (2006.01)
*A61F 2/46* (2006.01)
*A61F 2/30* (2006.01)

(52) U.S. Cl.
CPC .......... *A61F 2/4202* (2013.01); *A61F 2/4606* (2013.01); *A61F 2/468* (2013.01); *A61F 2/4684* (2013.01); *A61F 2/4657* (2013.01); *A61F 2002/3054* (2013.01); *A61F 2002/30329* (2013.01); *A61F 2002/30387* (2013.01); *A61F 2002/30392* (2013.01); *A61F 2002/30393* (2013.01); *A61F 2002/30398* (2013.01); *A61F 2002/30401* (2013.01); *A61F 2002/30433* (2013.01); *A61F 2002/30518* (2013.01); *A61F 2002/30537* (2013.01); *A61F 2002/30538* (2013.01); *A61F 2002/30542* (2013.01); *A61F 2002/4205* (2013.01); *A61F 2002/4207* (2013.01); *A61F 2002/4658* (2013.01); *A61F 2220/0025* (2013.01)

(58) Field of Classification Search
CPC ............ A61F 2002/30518–2002/30528; A61F 2002/30538–2002/30543; A61F 2002/30553–2002/30555; A61F 2/4202–2002/4207; A61F 2/4425–2002/443
See application file for complete search history.

(56) References Cited

U.S. PATENT DOCUMENTS

2004/0143332 A1*   7/2004   Krueger .............. A61B 17/025
                                                     623/17.14

* cited by examiner

*Primary Examiner* — Yashita Sharma
*Assistant Examiner* — Rebecca S Preston
(74) *Attorney, Agent, or Firm* — King & Spalding LLP (57) ABSTRACT

The invention relates to an ankle prosthesis (1) comprising a talar implant (2) designed to be implanted in or on the talus (3), a tibial implant (4) designed to be implanted in or on the tibia (5), and an intermediate implant (6) designed to be interposed between the tibial implant and the talar implant, said intermediate implant (6) being designed to be mounted to move relative to said talar implant (2) at a contact interface (7) in order to allow the ankle to move, said ankle prosthesis (1) being characterized in that it is provided with configurable coupling means (10) designed to enable the intermediate implant (6) to be arranged relative to the tibial implant (4) in a specific configuration chosen from among a plurality of possible configurations.

12 Claims, 2 Drawing Sheets

ANKLE PROSTHESIS WITH NEUTRAL POSITION ADJUSTMENT

This application is a continuation of U.S. patent application Ser. No. 11/553,252 filed Oct. 26, 2006, which is incorporated by reference in its entirety.

The present invention relates to the technical field of ankle prostheses designed to enable ankle joints to be treated orthopedically, and more particularly it relates to implants for restoring ankle joint anatomy, The present invention relates to an ankle prosthesis comprising a talar implant designed to be implanted in or on the talus, a tibial implant designed to be implanted in or on the tibia, and an intermediate implant designed to be interposed between said tibial implant and said talar implant, said intermediate implant being designed to be mounted to move relative to said talar implant at a contact interface in order to allow the ankle to move.

The present invention also relates to a method of preparing an ankle prosthesis as described above.

The present invention also relates to a test ankle prosthesis.

The present invention also relates to a surgical kit designed for putting an ankle prosthesis into place.

The present invention finally relates to a surgical method of implanting an ankle prosthesis comprising a talar implant designed to be implanted in or on the talus, a tibial implant designed to be implanted in or on the tibia, and an intermediate implant designed to be interposed between said tibial implant and said talar implant, said intermediate implant further being designed to be mounted to move relative to said talar implant at a contact interface in order to allow the ankle to move.

It is known that ankle prostheses can be used to restore a certain amount of freedom of movement to the joint of an ankle after said ankle has been damaged totally or partially, e.g. due to impact trauma or to disease.

In particular, it is known that an ankle prosthesis can be implanted that comprises three implants, namely a talar implant designed to be implanted in or on the talus (anklebone), a tibial implant designed to be implanted in or on the tibia, and an intermediate implant designed to be interposed between said tibial implant and said talar implant.

Generally, the intermediate implant has a large amount of freedom of movement between the other two implants. More particularly, it generally rests in plane abutment on the tibial implant so as to allow movements in anteroposterior translation, in mediolateral translation, and in rotation about the medullary axis of the tibia that is substantially perpendicular to the surface of said plane abutment.

Usually, the contact interface between the intermediate implant and the talar implant is constituted by a rounded friction surface that is generally cylindrical, spherical, or frustoconical in shape, in order to allow the leg to move in plantar flexion and in dorsal flexion relative to the leg.

Although they offer results that are advantageous in terms of movement, such ankle prostheses can however be unsuitable for the condition of the patient being treated.

When the patient has already undergone orthopedic treatment limiting the mobility of the ankle, the joint generally suffers from instability due to being weakened by muscle atrophy and/or to tendon laxity. Thus, when, for example, consideration is being given to performing arthroplasty (joint replacement) serving to restore joint mobility when the joint has been previously immobilized by arthrodesis (joint fusion), or indeed when it is desired to replace a prosthesis that is an old model and whose movement configuration differs from that of the three-implant prosthesis, suddenly restoring many degrees of freedom that have previously been lost tends to disturb the balance of the patient and exposes the patient to risks of falls, of injuries, and of damage to tissue situated at the joint in question.

Therefore, implementing prior art three-implant prostheses requires such patients to undergo a very long period of rehabilitation.

In addition, certain national regulatory requirements prohibit the use of prior art three-implant prostheses.

Objects assigned to the invention are therefore to propose a novel ankle prosthesis that does not suffer from the above-mentioned drawbacks and that, while offering satisfactory joint mobility, also guarantees good stability to the ankle joint.

Another object of the invention is to propose a novel ankle prosthesis that is ergonomic and comfortable in use for the patient.

Another object of the invention is to propose a novel ankle prosthesis in which wear is minimized and which offers increased longevity.

Another object of the invention is to propose a novel ankle prosthesis that is of particularly simple and robust design.

Another object of the invention is to propose a novel ankle prosthesis which is particularly easy to implement, and in particular to implant.

Another object of the invention is to propose a novel method of preparing an ankle prosthesis that imparts good stability to said ankle prosthesis.

Another object of the invention is to propose a novel method of preparing an ankle prosthesis that makes said prosthesis ergonomic.

Another object of the invention is to propose a novel test ankle prosthesis that makes it simpler and more reliable to implement an ankle prosthesis of the invention.

Another object of the invention is to propose a novel test ankle prosthesis that is of simple and inexpensive design.

Another object of the invention is to propose a surgical kit designed for putting an ankle prosthesis into place that, while offering satisfactory joint mobility, also guarantees good stability to the ankle joint, said kit enabling said ankle prosthesis to be implanted simply, accurately, and reliably.

Another object of the invention is to propose a novel surgical kit designed for putting an ankle prosthesis into place that is particularly simple in design and that is particularly easy to implement.

Another object of the invention is to propose a novel surgical method of implanting an ankle prosthesis that makes it possible to impart good stability and satisfactory mobility to the joint.

Another object of the present invention is to propose a novel surgical method of implanting an ankle prosthesis that, optimizes the longevity of the prosthesis and thus makes it more comfortable in use for the patient.

Finally, another object of the invention is to propose a novel surgical method of implanting an ankle prosthesis that can be implemented particularly simply, accurately, reliably, and reproducibly.

The objects assigned to the invention are achieved by means of an ankle prosthesis comprising a talar implant designed to be implanted in or on the talus, a tibial implant designed to be implanted in or on the tibia, and an intermediate implant designed to be interposed between the tibial implant and the talar implant, said intermediate implant being designed to be mounted to move relative to said talar implant at a contact interface in order to allow the ankle to move, said ankle prosthesis being characterized in that it is provided with configurable coupling means designed to enable the intermediate implant to be arranged relative to the tibial implant in a specific configuration chosen from among a plurality of possible configurations.

The objects assigned to the invention are also achieved by means of a method of preparing an ankle prosthesis comprising a talar implant designed to be implanted in or on the talus, a tibial implant designed to be implanted in or on the tibia, and an intermediate implant designed to be interposed between said tibial implant and said talar implant, said intermediate implant further being designed to be mounted to move relative to said talar implant at a contact interface, in order to allow the ankle to move, said method being characterized in that it includes an arrangement step (E1) during which the intermediate implant is arranged relative to the tibial implant, using configurable coupling means with which the prosthesis is provided, in a specific configuration that is chosen, during a selection step (E2), from among a plurality of possible configurations.

The objects assigned to the invention are also achieved by means of a test ankle prosthesis, characterized in that it is designed to be implanted temporarily in place of a final ankle prosthesis that can be configured in a specific configuration chosen from among a plurality of possible configurations, in that it is arranged so that it can, in vivo, take up any one of said possible configurations, and in that it is provided with reference means arranged to enable the practitioner to take the measurements of the configuration in which it finds itself so as to reproduce said configuration in the final ankle prosthesis.

The objects assigned to the invention are also achieved by means of a surgical kit designed for putting an ankle prosthesis into place, said surgical kit being characterized in that it comprises an ankle prosthesis referred to as a "final ankle prosthesis", and a test ankle prosthesis, both of which ate ankle prostheses of the invention.

The objects of the invention are also achieved by means of a surgical method of putting a "final ankle prosthesis" into place in a patient, said final ankle prosthesis comprising a talar implant designed to be implanted in or on the talus, a tibial implant designed to be implanted in or on the tibia, and an intermediate implant designed to be interposed between said tibial implant and said talar implant, said intermediate implant further being designed to be mounted to move relative to said talar implant at a contact interface in order to allow the ankle to move, said surgical method being characterized in that it comprises a step (a) for implanting a test ankle prosthesis, during which step a test ankle prosthesis comprising a test talar implant, a test tibial implant, and a test intermediate implant is implanted in the patient in place of the final ankle prosthesis, a determination step (b) during which a specific configuration of said test ankle prosthesis is determined in vivo from among a plurality of possible configurations, and a reproduction step (c) during which the specific configuration chosen during the determination step (b) is reproduced on the final ankle prosthesis by arranging the intermediate implant relative to the tibial implant by means of configurable coupling means.

The objects assigned to the invention are finally achieved by means of a surgical method of implanting a "final prosthesis" in a patient, said method being characterized in that it comprises an implantation step (K) for implanting a test prosthesis, during which step a test prosthesis that substantially reproduces the shape of the final prosthesis is implanted in the patient in place of the final prosthesis, a determination step (L) during which a particular operating configuration of said test prosthesis is determined in vivo from among a plurality of possible configurations, and a reproduction step (M) during which the particular operating configuration chosen during the determination step (L) is reproduced on the final prosthesis by means of fitting means with which said final prosthesis is provided.

Other characteristics and advantages of the invention will appear in more detail on reading the following description and on examining the accompanying drawings which are given merely by way of non-limiting illustration, and in which.

The ankle prosthesis 1 of the invention is designed to restore, at least partially, the mobility of an ankle joint in a patient who has in particular, suffered disease or impact trauma.

It can also be used to replace a previously implanted ankle prosthesis.

The ankle prosthesis 1 of the invention comprises a talar implant 2 designed to be implanted in or on the talus (anklebone) 3 and a tibial implant 4 designed to be implanted in or on the tibia 5.

The ankle prosthesis 1 further comprises an intermediate implant 6 which is designed to be interposed between the tibial implant 4 and the talar implant 2.

Said intermediate implant 6 is designed to be mounted to move relative to said talar implant 2 at a contact interface 7, in order to allow the ankle to move. Said intermediate implant 6 can, in particular, be made of polyethylene.

More precisely, the intermediate implant 6 preferably has a contact surface 6 A that is designed to come into abutment against a surface 2 A of the talar implant 2 that is of complementary shape, so that the intermediate implant can move by sliding, with friction, relative to the talar implant 2.

Most preferably, the complementary contact surfaces 2A, 6A are rounded in shape, e.g. substantially spherically, cylindrically or frustoconically rounded, so as to allow the foot to move in plantar flexion and in dorsal flexion relative to the leg.

According to an important characteristic of the invention, the prosthesis 1 is provided with configurable coupling means 10 designed to enable the intermediate implant 6 to be arranged relative to the tibial implant 4 in a specific configuration chosen from among a plurality of possible configurations.

In other words, the coupling means 10 make it possible to act on the prosthesis 1 in a manner such as to enable the practitioner to select that arrangement of the intermediate implant 6 relative to the tibial implant 4 which the practitioner deems most appropriate for each specific case and from among a plurality of potential choices.

The coupling means 10 that are configurable in the meaning of the invention make it possible to improve the stability of the prosthesis 1 and therefore the stability of the ankle joint, by keeping control over the relative mobility of the intermediate implant 6 and of the tibial implant 4, e.g. by setting limits for it.

In accordance with the invention, it is possible to imagine the coupling means 10 being designed merely to restrict the amplitude of movement in one or more of the freedoms allowed by the moving connection that it forms between the intermediate implant 6 and the tibial implant 4. For example, if the intermediate implant 6 is in plane abutment against the tibial implant 4, as in prior art three-implant prostheses, the coupling means 10 of the invention can include abutments or guide elements that limit the strokes in translation in the contact plane, e.g. in a manner such that the connection cannot be totally dislocated by uncontrolled movement over too large an amplitude.

However, the coupling means 10 are preferably designed to form a moving connection of the interfitting type between the intermediate implant 6 and the tibial implant 4. For this purpose, said configurable coupling means 10 preferably include engagement means 11 for engaging said intermediate implant 6 in said tibial implant 4.

Figures 1, 2, 3:
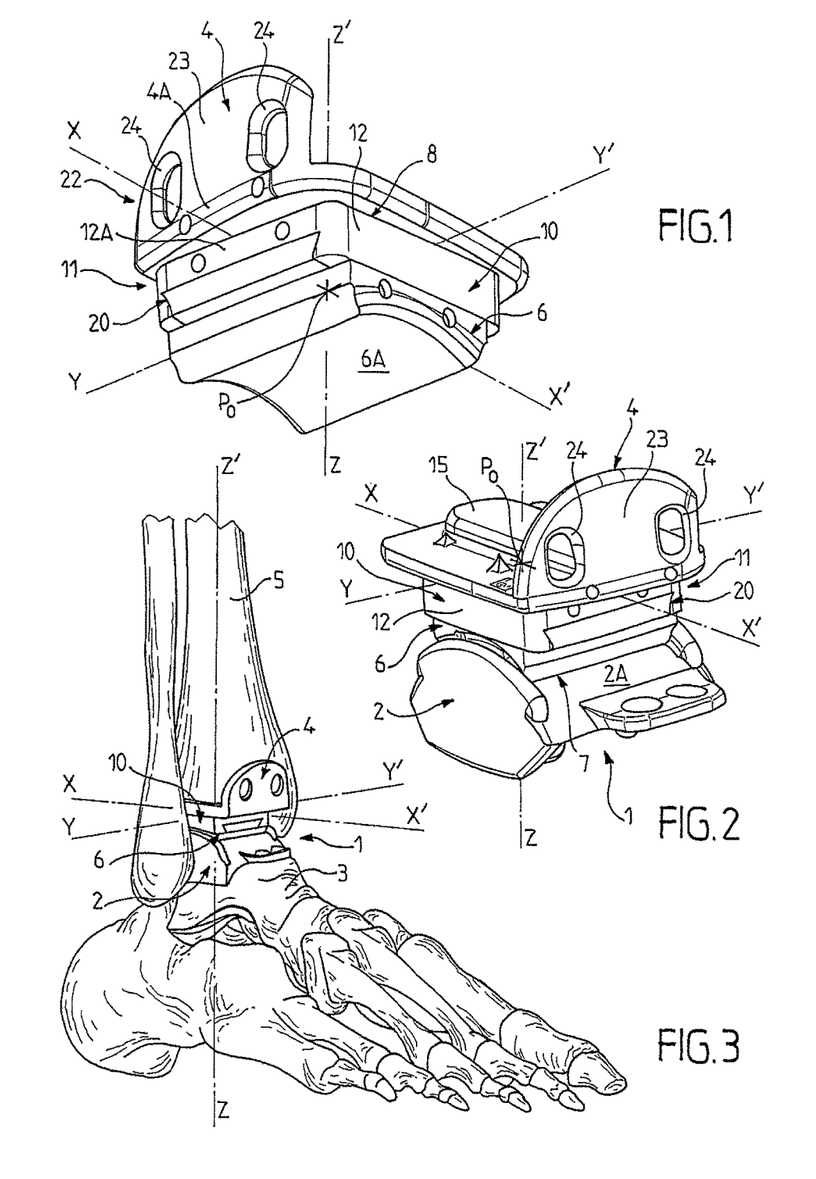
FIG. 1 is a perspective view of a portion of a variant embodiment of an ankle prosthesis of the invention.
FIG. 2 is a perspective view of an ankle prosthesis of the invention in which the portion shown in FIG. 1 is implemented.
FIG. 3 is a perspective view of the ankle prosthesis shown in FIG. 2 as implanted in the ankle joint.

Thus, in a preferred variant embodiment shown in particular in FIGS. 1 and 2, the coupling means 10 constitute fastening means designed to secure the intermediate implant 6 to the tibial implant 4.

Insofar as the coupling means 10 of the invention make it possible to restrain or even to prevent movements of the intermediate implant 6 relative to the tibial implant 4, mechanical stresses appear at said implants when the prosthesis 1 is involved in movements made by the patient, in particular during walking.

Such stresses can cause premature wear on any one of the components implants 2, 4, 6 of the prosthesis 1, or indeed can generate deformation or even breakage of said implants 2, 4, 6.

That is why, the specific configuration is preferably chosen as a function of the particular shape of the patients joint in which the prosthesis 1 is to be implanted. In other words, it is advantageously possible to adjust the prosthesis 1 of the invention as a function of the specific anatomy of the patient.

Most preferably, the specific configuration of the intermediate implant 6 relative to the tibial implant 4 is chosen such that the stresses exerted on the intermediate implant 6 and on the tibial implant 4 during the natural movements of the ankle are minimized overall. It is then referred to as the "neutral configuration"

More precisely, it should be recalled that, in a healthy person, the ankle joint allows the tibia 5 to move in a plurality of movements relative to the talus 3, and in particular, in addition to the dorsal flexion and plantar flexion movements:

a movement in anteroposterior translation substantially along an axis (XX'), when the leg tends to move "forwards" or "backwards" relative to the foot while said foot remains stationary;

a movement in mediolateral translation along an axis (YY') when the leg tends to move laterally inwards towards the patient's other leg or outwards away therefrom while said foot remains stationary; and a movement in rotation about the medullary axis (ZZ') of the tibia, when the leg tends to pivot through a yaw angle relative to the foot that remains stationary.

The three above-described movements are generally of small amplitude.

As shown in FIG. 3, when the patient is upright in the standing position and when the foot is resting on a flat and horizontal surface, the axis (XX') is substantially horizontal and parallel to the sagittal plane of the patient (i.e. said axis (XX') extends in the direction in which the patient is facing), the axis (YY') is substantially horizontal, extending towards one side of the patient, and substantially orthogonal to the axis (XX'), while the axis (ZZ') extends substantially vertically and forms a normal to the plane defined by the axes (XX') and (YY').

It is knower that, for each patient, as a function of his or her own specific anatomy, a point of origin $P_o$ exists about which the movements in anteroposterior translation, in mediolateral translation, and in rotation about the medullary axis (ZZ') of the tibia 5 take place. Geometrically, the point of origin $P_o$ substantially corresponds to the virtual intersection between the axes (XX'), (YY'), and (ZZ').

In addition, when a prosthesis 1 is implanted in the patient, said prosthesis, by construction, defines one or more movement axes which make it possible to restore, at least partially, one or more degrees of freedom for the joint.

The configuration that is neutral in the meaning of the invention thus corresponds to the intermediate implant 6 being in a position relative to the tibial implant 4 in which said intermediate implant 6 is substantially centered relative to the point of origin $P_o$ and in which the tibial implant 4 and/or the intermediate implant 6 is/are oriented such that the movement axes of the prosthesis 1 substantially coincide with the natural anatomical axes of the ankle of the patient.

By way of example, if the contact zone 8 between the intermediate implant 6 and the tibial implant 4 is arranged so as that they are in plane abutment, said contact zone 8 should be substantially normal to the axis (ZZ') and located in the immediate vicinity of the translation axes (XX') and (YY'), and preferably superposed on the plane formed by said translation axes.

For reasons of convenience, in the description below, the expression "neutral configuration" applies to the prosthesis 1 as a whole, or to the coupling means 10, or to any other component element of the prosthesis 1 when said prosthesis is considered in the situation in which it finds itself when the arrangement of the intermediate implant 6 relative to the tibial implant 4 corresponds to the neutral configuration.

Particularly advantageously, by offering the possibility of placing the intermediate implant 6 in the neutral configuration, the configurable coupling means 10 of the invention make it possible to minimize the amplitude of any residual movements of said intermediate implant 6 relative to said tibial implant 4 and/or to limit the stresses exerted on these elements when said implants 4, 6 are secured to each other.

In addition, this possibility of adjustment offered by the coupling means 10 advantageously makes it possible to adapt the prosthesis 1 to fit the shape of the joint that is specific to each patient, thereby enabling said prosthesis 1 to be adjusted finely, accurately, and in personalized manner.

It is thus possible to prevent, to a large extent, discomfort in use and excessive wear that would inevitably result from arbitrary restriction of the intermediate implant 6 on the tibial implant 4 in a single configuration that is pre-determined by construction in the prosthesis itself, and that would not always correspond to the anatomy of the patient in question.

In a preferred variant embodiment shown, in particular, in FIGS. 1, 2, 5, 6, and 7, the configurable coupling means 10 include a base 12 designed to be fastened to the tibial implant 4 and to form a mechanical interface between said tibial implant 4 and the intermediate implant 6.

Said base 12 is preferably substantially in the shape of a rectangular block.

Preferably, said base 12 is provided with adjustable fastening means 14 which make it possible to choose, from among a plurality of possible positions, that position in which said base 12 is actually fastened relative to the tibial implant 4.

Naturally, the configuration of the contact zone 8 between the tibial implant 4 and the base 12 is not limited to one particular embodiment. However, the contact zone between the tibial implant 4 and the base 12 is preferably substantially plane and, more preferably, it coincides substantially with the plane defined by the axes (XX') and (YY').

Thus, it is advantageously possible to press the base 12 against the tibial implant 4 and to position it relative thereto in a wide variety of positions and of orientations, by using the degrees of freedom offered by the resulting free plane abutment connection. Final fastening, for locking the base 12 firmly, can then take place, after the neutral configuration has been identified.

In a preferred variant embodiment, the adjustable fastening means 14 enable the position in which the base 12 is fastened relative to the tibial implant 4 to be adjusted continuously, e.g. by means of a screw co-operating with an oblong hole or by means of any other suitable mechanism.

Figures 4, 5:
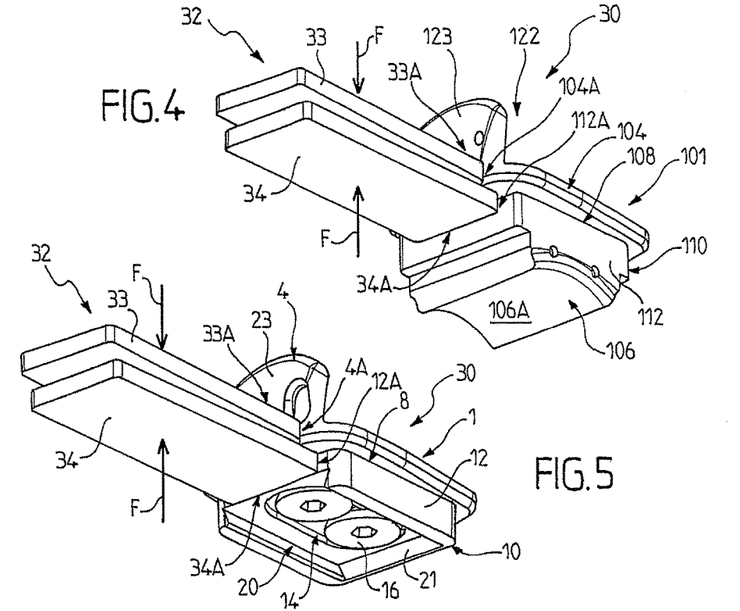
FIG. 4 is a perspective view of implementation of a first portion of a surgical kit of the invention.
FIG. 5 is a perspective view of implementation of a second portion of a surgical kit of the invention.
Figures 6, 7:
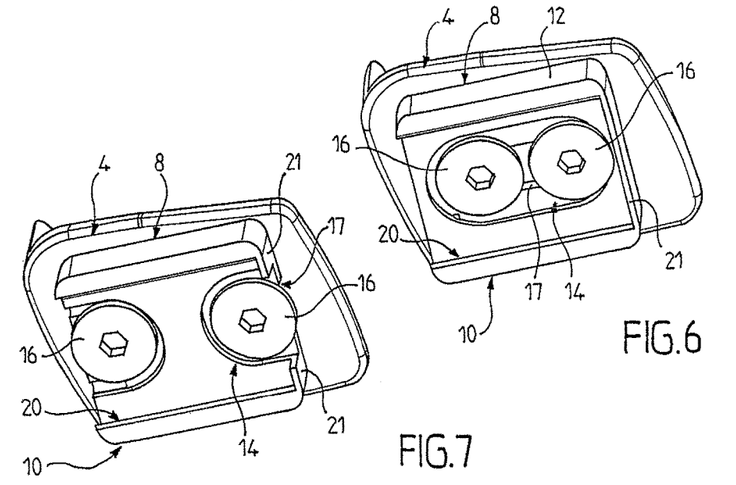
FIG. 6 is a perspective view of a variant embodiment of a tibial implant and of coupling means in an ankle prosthesis of the invention.
FIG. 7 is a perspective view of another variant embodiment of a tibial implant and of coupling means in an ankle prosthesis of the invention.

In particular, as shown in FIGS. 5 to 7, the adjustable fastening means 14 can comprise a plurality of broad-headed screws 16 co-operating with one or more grooves 17 provided in the base 12 and dimensioned such that the residual clearance between the shanks of the screws 16 and the edges of the grooves 17 makes it possible to adjust the position of said base 12 linearly or angularly relative to the tibial implant 4. Thus, it is possible firstly to couple the base 12 loosely to the tibial implant 4, and then to adjust its position, and finally to tighten the screws 16 in order to press said base 12 and to hold it stationary against the tibial implant 4. A projection 15, as shown in FIG. 2, can also be provided on the tibial implant 4 firstly so as to provide a reference element enabling said tibial implant 4 to be positioned mediolaterally in reproducible manner relative to the tibia 5, and secondly so as to impart to the tibial implant 4 the thickness of material that is required by the use of the screws 16.

In a preferred variant embodiment, the base 12 is provided with reception means 20 making it possible to connect the intermediate implant 6 to said base 12.

Most preferably said reception means 20 are arranged so that the intermediate implant 6 can occupy only a single and predetermined position relative to the base 12.

Various solutions can be devised for implementing such reception means 20, and in particular tongue-and-groove systems or systems having screws, such systems preferably being associated With keying means such as centering studs, notches, or lugs.

In a preferred variant embodiment shown in particular in FIGS. 1, 2, and 5, the reception means 20 are formed by a dovetail, it then being possible for the intermediate implant 6 to be inserted by being slid laterally into the base 12.

In this variant, it suffices to lock the intermediate implant in translation along the generator axis of the dovetail in order to obtain an interfitting connection between said base 12 and said intermediate implant 6.

Preferably, an abutment element 21 is provided against which the intermediate implant 6 comes into abutment when it is inserted fully into the base 12, and non-return means (not shown) are provided that oppose extraction of the intermediate implant 6 from the base 12 after said intermediate implant has been inserted into said base.

In a manner well known to the person skilled in the art, such non-return means can, for example, be formed by snap-fastening, in particular by means of a moving lip projecting from one of the faces of the intermediate implant 6 that come into contact, with the base 12, said lip deforming elastically or retracting while the intermediate implant 6 is being inserted into the base 12 and then re-deploying into a notch provided for that purpose in said base once said intermediate implant has reached its abutment position.

Thus, according to the invention, the engagement means 11 for engaging the intermediate implant 6 into the tibial implant 4 can advantageously be formed by the combination of the base 12, of its adjustable fastening means 14 and of its reception means 20.

It is remarkable that, once in position in the dovetail, the intermediate implant 65 can advantageously serve to lock the heads of the fastening screws 16, thereby preventing any untimely appearance of slack between the base 12 and the tibial implant 4 due to said screws 16 coming loose accidentally.

In a preferred variant embodiment, the ankle prosthesis 1 further comprises reference means 22 designed to indicate how the intermediate implant 6 is arranged relative to the tibial implant 4 in order to enable the practitioner to configure the configurable coupling means 10 accurately. In other words, said reference means 22 inform the practitioner of the configuration in which the configurable coupling means 10, and more generally the prosthesis 1, find themselves.

More particularly, the reference means 22 of the invention can constitute three-dimensional reference means designed to inform the practitioner of how the intermediate implant 6 and/or the base 12 is/are disposed relative to the tibial implant 4.

Thus, it is advantageously possible to know, and therefore, as described in detail below, to reproduce, the arrangement of the prosthesis 1 that corresponds to a particular configuration, in particular the neutral configuration.

Preferably, the reference means 22 comprise a first reference surface 4A associated with the tibial implant 4 and a second reference surface 12A associated with the base 12, the relative position of said first and second reference surfaces 4A, 12A thus making it possible to determine and more generally to indicate, both visually and physically, the position of said base 12 in the frame of reference formed by the tibial implant 4.

In a preferred variant embodiment, the tibial implant 4 has a tongue 23 that forms both a tibial shield preventing excessive development of bone cells that could hinder operation of the joint, and also a fastening tab provided with oblong holes 24 that serve to receive screws for fastening to the bone. The first reference surface 4A can then advantageously be formed by a sector of the anterior face of the tongue 23 that is preferably substantially plane, In analogous manner, the second reference surface 12A is preferably formed by a substantially plane face of the base 12.

Advantageously, as described in detail below, the first and second reference surfaces 4A, 12A make it possible to adjust the position of the base 12 accurately relative to the tibial implant 4 during assembly of the prosthesis 1.

The present invention also relates to a method of preparing an ankle prosthesis 1 comprising a talar implant 2 designed to be implanted in or on the talus 3, a tibial implant 4 designed to be implanted in or on the tibia 5, and an intermediate implant 6 designed to be interposed between said tibial implant 4 and said talar implant 2, said intermediate implant 6 further being designed to be mounted to move relative to said talar implant 2 at a contact interface 7, in order to allow the ankle to move, said method being characterized in that it includes an arrangement step (E1) during which the intermediate implant 6 is arranged relative to the tibial implant 4, using configurable coupling means 10 with which the prosthesis 1 is provided, in a specific configuration that is chosen, during a selection step (E2), from among a plurality of possible configurations.

Preferably, during the selection step (E2), the specific configuration is chosen as a function of the particular shape of the patient's joint in which the prosthesis 1 is to be implanted, and, more preferably, the neutral configuration that is specific to said patient is chosen as the specific configuration.

In a first variant, said preparation method can advantageously be implemented in the factory, as an assembly step of a method of manufacturing a made-to-measure ankle prosthesis that is to be delivered pre-assembled in the neutral configuration.

It is possible, in particular, to imagine that a hospital practitioner can, after having performed a diagnostic and having taken biometric measurements on the patient, e.g. by medical imaging, remotely order a prosthesis 1 from the manufacturer for a future operation, merely by transmitting to said manufacturer the dimensional specifications including the key data relating to assembly of the component elements of the prosthesis, and by leaving said manufacturer to perform the appropriate assembly and packaging of said prosthesis.

In another variant, said preparation method can be implemented during a surgical operation by the surgeon, during which the surgeon personally configures the prosthesis 1 at the time of implantation thereof.

The present invention also relates to a test ankle prosthesis 101 designed to be implanted temporarily in place of a final ankle prosthesis that can be configured in a specific configuration chosen from among a plurality of possible configurations, said test ankle prosthesis firstly being arranged so that it can, in vivo, take up any one of said possible configurations, and secondly being provided with reference means 122 arranged to enable the practitioner to take the measurements of the configuration in which it finds itself so as to reproduce it in the final ankle prosthesis.

In the meaning of the invention, the test ankle prosthesis 101 and the final ankle prosthesis are preferably designed to be used during a single surgical operation, the test ankle prosthesis firstly being put into place in the ankle joint in order to enable the neutral configuration that is specific to the patient to be identified and referenced, an then being removed and replaced with the final ankle prosthesis 1 whose intermediate implant 6 is positioned and fastened to the tibial implant 4 as a function of the result of the three-dimensional referencing of the neutral configuration that is performed on the test ankle prosthesis 101.

In other words, the test ankle prosthesis 101 preferably constitutes an intermediate implantation accessory that makes it possible, in the patient, to take the topographical measurements necessary for the final ankle prosthesis to be in the correct configuration, and said test ankle prosthesis is not an operational prosthesis designed to remain durably in the joint and to withstand stresses related to walking.

Advantageously, the test ankle prosthesis 101 can thus present a structure that is simplified compared with the final ankle prosthesis, and in particular, that can be implemented using materials that are less strong and less expensive than the materials used for the final ankle prosthesis.

Preferably, the final ankle prosthesis is formed by an ankle prosthesis 1 as described above, and the test ankle prosthesis 101 comprises a test talar implant 102, a test tibial implant 104, a test intermediate implant 106 and test configurable coupling means 110 whose shapes and dimensions correspond substantially to the shapes and dimensions respectively of the talar implant 2, of the tibial implant 4, of the intermediate implant 6, and of the configurable coupling means 10.

By numbering convention, the references given to the component elements of the test ankle prosthesis 101 correspond to the references of the analogous component elements of the final ankle prosthesis plus 100.

In a preferred variant embodiment, the test intermediate implant 106 and the test configurable coupling means 110, and more precisely the test base 112 thereof form a one-piece unit of the block type 106, 110, as shown in FIG. 4.

To this end, it is remarkable that, in accordance with the present invention, it is not absolutely necessary to reproduce the configurable coupling means 10 exactly on the test ankle prosthesis 101.

If it is decided to opt for a variant embodiment of the final ankle prosthesis 1 in which the intermediate implant 6 can take up only one position relative to the base 12, firstly it is necessary and sufficient, in order to define the neutral configuration completely, to know merely the position of one or the other of these two elements relative to the tibial implant 4.

Secondly, insofar as only the mobility of the test intermediate implant 106 relative to the test tibial implant 104 is then of interest in seeking the appropriate position that is to be imparted to the base 12, it is not essential to provide the equivalent of the fastening means 14 on the test ankle prosthesis 101.

It is thus advantageously possible, in the test ankle prosthesis 101, to model said unit formed by the base 12 and by the intermediate implant 6, which unit can be likened dynamically to a single solid, by a block 106, 110 reproducing merely the outside working dimensions and shapes of said unit.

In a particularly preferred variant embodiment, that surface of the block 106, 110 which is designed to come into contact with the test tibial implant 104, at the contact zone 108, is substantially plane, smooth, and without any fastening means.

Naturally, other simplifications of the component elements of the test ankle prosthesis 101 can be made relative to their counterparts in the final ankle prosthesis 1 without going beyond the ambit of the present invention, providing that said simplifications are not detrimental to the feasibility and to the validity of determining the neutral position.

Such simplifications, associated with the use of inexpensive materials advantageously make it less expensive to produce a test ankle that is suitable for being sterilized and used a plurality of times.

In addition, the test ankle prosthesis 101 of the invention can advantageously be provided with self-centering means arranged so as to bring said test ankle prosthesis into a neutral configuration, in which the stresses exerted on the test intermediate implant 106 and on the test tibial implant 104 during natural movements of the ankle are minimized overall. In other words, said self-centering means spontaneously tend to place said test ankle prosthesis 101 in a neutral configuration, preferably under the effect of natural movements that the surgeon imparts to the foot of the patient relative to the leg of the patient.

To this end, the self-centering means are preferably formed by the block 106, 110 itself, which is then arranged so as to be interposed freely between the test talar implant 102 and the test tibial implant 104 in a manner such as to find itself firstly in plane abutment connection therewith, at the contact interface 8, and more particularly in the plane defined by the axes (XX') and (YY'), and secondly in preferably sliding pivotal connection with the test talar implant 102, at its rounded surface 106A.

Such an arrangement imparts self-centering behavior to the block 106, 110 due to the fact that, when the test ankle prosthesis 101 is implanted and when the block 106, 110 finds itself positioned between the test tibial implant 104 and the test talar implant 102, in contact with those implants via opposite ones of its faces, the surgeon, by manipulating the foot relative to the leg, can, under the effect of the dynamic stresses generated in the joint, cause said block 106, 110 to be moved progressively through the degrees of freedom allowed by the plane abutment, until said block reaches a position that is substantially centered on the position of origin $P_o$ in which the state of the dynamic stresses is minimized overall.

Preferably, the reference means 122 are arranged so as to co-operate with the touch-sensitive members 33, 34 of measurement means 32 designed to enable the practitioner to take the measurements of the configuration of the test ankle prosthesis 101 when said ankle prosthesis finds itself implanted in the patient.

Most preferably, said reference means 122 are arranged so as to be secured to said touch-sensitive members 33, 34 prior to implantation of said test ankle prosthesis, so as to be capable of co-operating therewith while the test ankle prosthesis is implanted. Thus, it is possible, in particular, to obtain continuous monitoring of changes in the configuration in which the test ankle prosthesis finds itself in vivo.

To this end, it is remarkable that the dimensional and functional mimicry existing between the test ankle prosthesis 101 and the final ankle prosthesis 1 advantageously enables the practitioner to take the position measurements directly on said test ankle prosthesis 101, the distances and the orientations of the component elements of said test ankle prosthesis faithfully expressing the configuration that should be reproduced with the final ankle prosthesis 1.

The present invention also relates to a surgical kit 30 that is designed for putting an ankle prosthesis into place.

According to the invention, said surgical kit 30 comprises an ankle prosthesis 1 of the invention, referred to as a "final ankle prosthesis", and a test ankle prosthesis 101 as described above.

Preferably, the surgical kit 30 of the invention further comprises measurement means 32 designed to enable the practitioner to take the measurements of the configuration of the test ankle prosthesis 101 while said test ankle prosthesis 101 is implanted in the patient.

More precisely, said measurement means 32 are preferably designed to take the measurements of the position of the test coupling means 110, or of the block 106, 110, relative to the test tibial implant 104, in particular when the test ankle prosthesis 101 is in the neutral configuration so that the stresses exerted on the intermediate implant 106 and on the tibial implant 104 during the natural movements of the ankle are minimized overall.

The measurement means 32 of the invention can use either contact measurement technology of the feeler type, or remote measurement technology of the laser beam type. It is also possible to use explicit measurement, e.g., by enabling the practitioner to quantify a linear offset (in millimeters) and/or an angular offset (in degrees) of the block 106, 110 relative to the tibial implant 104, or indeed, preferably, to use an implicit measurement of the neutral configuration by shaping a template that gives the relative position of these elements.

Preferably, the measurement means 32 comprise a first touch-sensitive member 33 presenting a first feeler surface 33A and a second touch-sensitive member 34 presenting a second feeler surface 34A, the feeler surfaces being designed to come into contact respectively with the test tibial implant 104 and with the test intermediate implant 106.

More precisely, as shown in FIG. 4, the second feeler surface 34A is preferably arranged to come into contact with the test base 112 that forms the bottom of the block 110.

In a preferred variant embodiment, the first and second touch-sensitive members 33, 34 are provided with association means for associating them respectively with the test tibial implant 104 and with the test intermediate implant 106 so that it is possible firstly for them to be secured to the respective ones of these implants prior to implantation of the test ankle prosthesis 101 and secondly for them to remain secured to said implants while said test ankle prosthesis 101 is inside the patient.

In particular, for this purpose, it is possible to use a system of pegs that project from the feeler surfaces and that are designed to fit into holes provided in first and second test reference surfaces 104A, 112A associated respectively with the test tibial implant 104 and with the base 112 of the block 106, 110.

Thus, the measurement means 32 of the invention are suitable for continuously evaluating the configuration of the implanted test ankle prosthesis 101 by monitoring, in real time, the movements of the test intermediate implant 106 relative to the test tibial implant 104.

Preferably, the association means are arranged so as to enable each of the touch-sensitive members 33, 34 to be aligned with and to be fastened to the test reference surface 104A, 112A that is associated with it in a single and reproducible position.

Preferably, the first and second touch-sensitive members are formed respectively by first and second extension leaves, each of which has one end that, when the test ankle prosthesis 101 is implanted, projects from the incision made to access the ankle of the patient.

Most preferably, as shown in FIGS. 4 and 5, each of the first and second touch-sensitive member 33, 34 is formed of a rectangular plate, the two plates advantageously being suitable for being associated with each other to form a free plane abutment connection that is co-planar with the contact zone 8, 108, i.e. that is co-planar with the plane formed by the axes (XX') and (YY') when the test ankle prosthesis 101 is implanted.

Preferably, the first and second touch-sensitive members 33, 34 are coupled together by reversible or releasable locking means so that they can be allowed to move relative to each other or else be constrained to move with each other.

In a particularly preferable variant embodiment shown in FIGS. 4 and 5, the two touch-sensitive members 33, 34 can be constrained to move with other simply and reliably by means of vise-grip pliers (not shown) that tend to compress them one against the other, at the portion that projects beyond the incision, by exerting a clamping force F that is substantially normal to the contact plane 108.

Thus, implementing the reversible locking means does not disturb the positions of the first and second touch-sensitive members 33, 34 or of the test tibial implant 104, or of the block 106, 110 once the neutral configuration is reached by the test ankle prosthesis 101.

Preferably, the first and second test reference surfaces 104, 112 are substantially identical respectively to the first and second reference surfaces 4, 12 of the final ankle prosthesis 1 so that the first and second touch-sensitive members 33, 34 can engage similarly and equally well the final tibial implant 4 and the test tibial implant 104, or the final base 12 and the test base 12.

In addition, the final ankle prosthesis 1 preferably has elements complementary to the association means for association with the test tibial implant 104 and with the test intermediate implant 106, in particular holes designed to receive the pegs on the touch-sensitive members 33, 34.

Thus, the test ankle prosthesis 101 and the final ankle prosthesis 1 are interchangeable so that, after referencing the neutral configuration on the test ankle prosthesis, after fastening the touch-sensitive members 33, 34 together, and after disengaging said touch-sensitive members from the test ankle prosthesis 101, it is possible to place the tibial implant 4 and the base 12 so that they are respectively touching the first and second feeler surfaces 33A, 34A, and thus to position these elements in the neutral configuration.

In other words, the measurement means 32 of the invention are preferably also designed to enable the configuration of the test ankle prosthesis 101 to be transposed to the final ankle prosthesis 1, said measurement means 32 forming an assembly template for said final ankle prosthesis 1.

It is remarkable that such a preferred variant embodiment of the measurement means 32 makes it possible for said configuration to be transposed rapidly, simply, and accurately, the measurement taken on the test ankle prosthesis 101 and its reproduction on the final ankle prosthesis 1 taking place immediately and intuitively without it being necessary for the practitioner to seek to know explicitly any intermediate value, such as a linear or angular offset.

Naturally, the present invention can concern the measurement means 32 considered separately in their own right, and more precisely an adjustable template making it possible to take the physical measurements of a particular configuration taken up by the test ankle prosthesis 101 so as to transpose that configuration onto the final ankle prosthesis1.

In accordance with the invention, the final ankle prosthesis 1 can thus advantageously be assembled outside the operating drape, on an accessory workstation, under conditions that are particularly easy and practical, in particular in terms of accessibility, lighting, cleanness, etc.

Furthermore, in a variant embodiment of the kit 30 of the invention, the final talar implant 2 also serves as the test implant 102, and, by being put into place directly, it advantageously limits the trauma suffered by the talus by sparing said talus the replacement of one implant with another. For reasons of clarity, reference is however made in the present description to a "test talar implant 102" in order to designate the final talar implant 2 when it is used as an element of the test ankle prosthesis 101 for evaluating the configuration in which the final ankle prosthesis 1 is to be implanted.

It is also remarkable that, by giving the test tibial implant 104 mediolateral and anteroposterior centering structures that are homologous to the those of the final tibial implant 4, namely respectively a projection (not shown) and a tibial shield 123, it is possible to position the final tibial implant 4 relative to the tibia 5 immediately in a position identical to the position previously occupied by the test tibial implant 104.

Naturally, the surgical kit of the invention is not limited to implanting an ankle prosthesis and it can be supplied in other forms for implementing other prostheses, in particular joint prostheses. The person skilled in the art can naturally determine the appropriate dimensioning and shapes for the component elements of the final prosthesis and of the test prosthesis resulting from such an adaptation.

The present invention also relates to a surgical method of putting a "final ankle prosthesis" into place in a patient, said final ankle prosthesis 1 comprising a talar implant 2 designed to be implanted in or on the talus, a tibial implant 4 designed to be implanted in or on the tibia 4, and an intermediate implant 6 designed to be interposed between said tibial implant and said talar implant, said intermediate implant 6 further being designed to be mounted to move relative to said talar implant 2 at a contact interface 7 in order to allow the ankle to move.

Most preferably, said method can be implemented using a surgical kit 30 as described above, to which reference is made by way of a particular example.

According to the invention, the surgical method includes a step (a) for implanting a test ankle prosthesis, during which step a test: ankle prosthesis 101 comprising a test talar implant 102, a test tibial implant, and a test intermediate implant 106 is implanted in the patient in place of the final ankle prosthesis.

More precisely, after preparing the bone surfaces in question, in particular by resection, the practitioner mounts and temporarily fastens the test talar implant 102 in or on the talus 3 and the test tibial implant 104 in or on the tibia 5. The practitioner then roughly positions the block 106, 110 in the joint, by interposing said block between the test tibial implant 104 and the test talar implant 102, so that firstly its surface 106 A comes into contact with the surface 102 A of the test talar implant so that it can slid thereon with friction, and secondly so that its opposite surface comes into free plane abutment against the test tibial implant 104 at the contact zone 108.

The surgical method of the invention also includes a determination step (b) during which a specific configuration of said test ankle prosthesis is determined in vivo from among a plurality of possible configurations.

Preferably, during the determination step (b), a "neutral configuration" is identified empirically as the specific configuration of the test ankle prosthesis 101, in which neutral configuration the stresses exerted on the test ankle prosthesis 101 during natural movements of the ankle joint are minimized overall.

Most preferably, the determination step (b) for determining the specific configuration comprises a patient manipulation sub-step (b1) during which said patient is placed in a predetermined posture so as to observe the behavior of the test ankle prosthesis (101) under the effect of said manipulation, and an adjustment sub-step (b2) during which the configuration of the test ankle prosthesis (101) is modified as a function of the behavior observed during the sub-step (b1).

More particularly, the practitioner can force the foot to move relative to the leg, in particular by causing it to undergo plantar flexion followed by dorsal flexion in order to observe the response from the block 106, 110 to these manipulations.

Preferably, during the determination step (b), a plurality of manipulation sub-steps (b1) are performed successively, each of which is followed by a adjustment sub-step (b2) so as to adjust the configuration of the test ankle prosthesis 101 iteratively, The practitioner can, in particular, put the patient cyclically through a plurality of distinct postures in a determined sequence, and, for example, alternate dorsal flexions and plantar flexions repetitively.

Advantageously, under the effect of the manipulations of the joint, the block 106, 110 tends spontaneously to become centered on the position $P_o$ in which the stresses to which it is subjected during the movements of the joint are substantially minimized.

In other words, the manipulation sub-step (1) and the adjustment step (2) preferably coincide with each other, the test ankle prosthesis 101 being designed to be self-configuring in response to one or more manipulations of the patient.

Thus, the surgeon can, by constraining the block 106, 110 to migrate iteratively by means of successive manipulations of the foot relative to the leg, cause the test ankle prosthesis 101, and more particularly said block 106, 110 to converge progressively towards its neutral configuration.

The surgical method of the invention further includes a reproduction step (c) during which the specific configuration chosen during the determination step (b) is reproduced on the final ankle prosthesis 1 by arranging the intermediate implant 6 relative to the tibial implant 4 by means of configurable coupling means 10.

Preferably, since the entire method is applied during a single surgical operation, said method includes a replacement step (d) during which the test ankle prosthesis 101 is extracted and the final ankle prosthesis 1 as placed in the chosen specific configuration is implanted in place of said test ankle prosthesis.

To this end, it is remarkable that said replacement step (d) can concern all or part of the test ankle prosthesis, it being possible, for example, for the test talar implant 102 to be kept and used as the final talar implant 2.

Preferably, the surgical method includes a preparation step (e) for preparing the test ankle prosthesis 101, during which step, the test ankle prosthesis is associated with measurement means 32 designed to enable the practitioner to take the measurements of the configuration of the test ankle prosthesis 101 while said test ankle prosthesis is implanted in the patient.

The preparation step (e) can advantageously be performed prior to the implantation step (a) for implanting the test ankle prosthesis 101, so that it is possible to monitor continuously the changes in the configuration of said test ankle prosthesis and so as to collect at any time the data that is characteristic of the positioning of the test intermediate implant 106 relative to the test tibial implant 104.

Preferably, since the measurement means 32 are provided with one or more touch-sensitive members 33, 34, each of which is designed to feel the test ankle prosthesis 101, the reproduction step (c) includes a sub-step (c1) for locking the measurement means 32, during which sub-step the positions of said touch-sensitive members 33, 34 are locked by reversible locking means.

More precisely, with the measurement means 32 comprising a first touch-sensitive member 33 presenting a first feeler surface 33A and a second touch-sensitive member 34 presenting a second feeler surface 34A designed to come into contact respectively with the test tibial implant 104 and with the test intermediate implant 106 , the locking sub-step (c1) is performed by fastening the first and second touch-sensitive members to each other.

Most preferably, the practitioner holds the rectangular extension leaves forming touch-sensitive members 33, 34 stationary by compressing them against each other by means of vise-grip pliers when he or she considers that the test ankle prosthesis 101 has reached the neutral configuration under the effect of the manipulations performed during the determination step (b). The practitioner can thus take the configuration measurements and store the collected information durably.

Advantageously, implementing the measurement means 32 does not interfere with the test ankle prosthesis 101, and in particular does not cause any uncontrolled accidental movement of the block 106, 110 once the neutral configuration is reached.

The reproduction step (c) preferably also includes a fitting sub-step (c2) during which the final ankle prosthesis 1 is configured by means of an assembly template established on the basis of the data collected by the measurement means .

More precisely, the fitting sub-step (c2) can comprise a first stage (c'2) subsequent to the locking step (c1), and during which the assembly formed by the touch-sensitive members 33, 34, which are still fastened together, is separated from the test ankle prosthesis 101, and a second stage (c"2) during which the final tibial implant 4 is brought into abutment against the first feeler surface 33A, and the coupling means 10, and more particularly the base 12 thereof, are/is brought into abutment against the second feeler surface 34A, the touch-sensitive members thereby forming the assembly template for the final ankle prosthesis 1, as shown in FIG. 5.

Advantageously, the final ankle prosthesis 1 can thus be configured on an uncluttered workstation prior to implantation.

Preferably, during the second stage (c"2), the practitioner places the base 12 so that it is touching the tibial implant 4 at the contact zone 8 and engages the screws 16 without tightening them, and then applies the respective reference surfaces 4A, 12A of the tibial implant and of the base against the touch-sensitive members 33, 34 forming the assembly template so that they are put into place spontaneously. Once the base 12 is positioned, the practitioner tightens the screws 16 and then inserts the intermediate implant 6 in the base 12 by engaging it into abutment in the dovetail.

Thus, the practitioner can easily transfer to the final ankle prosthesis 1 a specific configuration that is specific to the patient, and that is determined empirically on the test ankle prosthesis 101 in order to match as well as possible the joint shape of said patient.

Naturally, the present surgical method is in no way limited to implanting an ankle prosthesis.

In particular, it can constitute a surgical method of implanting a "final prosthesis" in a patient, said method comprising an implantation step (K) for implanting a test prosthesis, during which step a test prosthesis that substantially reproduces the shape of the final prosthesis is implanted in the patient in place of the final prosthesis, a determination step (L) during which a particular operating configuration of said test prosthesis is determined in viva from among a plurality of possible configurations, and a reproduction step (M) during which the particular operating configuration chosen during the determination step (L) is reproduced on the final prosthesis by means of fitting means with which said final prosthesis is provided.

The term "operating configuration" is used to mean both the static three-dimensional layout (shapes, volumes, positions, and orientations of the various component elements of the prosthesis) and the arrangements for motion (degrees of freedom) that are implemented during normal operation of the final prosthesis.

In the meaning of the invention, the final prosthesis and the test prosthesis can each intrinsically take up a plurality of operating configurations, each operating configuration of the final prosthesis having its counterpart or "homologue" (i.e. in the concept of mathematical sets terminology, its "antecedent") on the test prosthesis. The method of the invention thus aims to "adjust" the final prosthesis by previously putting the test prosthesis in situ in order to seek the most suitable operating configuration.

To this end, the test prosthesis of the invention substantially reproduces the shapes and/or the moving connections of the final prosthesis. It is also designed to be implanted and then replaced with the final prosthesis in a single surgical operation.

Said surgical method is particularly applicable to putting a joint prosthesis into place in a joint, which prosthesis aims to impart a certain amount of mobility to said joint.

Most preferably, during the determination step (L), a "neutral configuration" is identified empirically as the particular operating configuration of the test prosthesis, in which neutral configuration the stresses exerted on the test prosthesis during the natural movements of the joint are minimized overall.

Preferably, for this purpose, the determination step (L) comprises a patient manipulation sub-step (L1) during which said patient is placed in a predetermined posture so as to make it possible to observe the behavior of the test prosthesis under the effect of said manipulation, and an adjustment sub-step (L2) during which the configuration of the test prosthesis is modified as a function of the behavior observed during the manipulation sub-step (L1).

Preferably, said method further comprises a preparation step (O) for preparing the test prosthesis, during which step the test prosthesis is associated with measurement means designed to enable the practitioner to take the measurements of the configuration of the test prosthesis while it is implanted inside the patient.

Thus, particularly advantageously, the prosthesis 1 of the invention offers an excellent compromise between joint stability, which facilitates the rehabilitation of the patient, in particular in cases of tendon laxity and muscle atrophy, comfort in use, related in particular to the reduced sensation of hindrance, and longevity due to the fact that said prosthesis is subject to only a small amount of wear.

Advantageously, the ankle prosthesis and the methods of the invention make it possible to personalize the orthopedic treatment for each patient, while also preserving a structure that is simple, and an implementation that is particularly easy and reliable.

The invention claimed is:

1. An ankle prosthesis component for use with an ankle, comprising:
an intermediate implant configured to be disposed between a tibia implant and a talar implant, the intermediate implant comprising a top portion and a bottom portion, the bottom portion defining a curved surface configured to move relative to the talar implant at a contact interface and the top portion being configured to couple to the tibia implant such that the intermediate implant can rotate relative to the tibia about a first axis so as to position the intermediate implant at an angle relative to the tibia implant and can lock relative to the tibia implant thereby impeding rotation relative to the tibia implant once positioned and such that the intermediate implant can move linearly along a second axis which is substantially normal to the first axis and can lock relative to the tibia thereby impeding linear movement along the second axis once positioned.

2. The ankle prosthesis component according to claim 1, wherein the first axis is a medullary axis (ZZ') of the tibia.

3. The ankle prosthesis component according to claim 2, wherein the angle corresponds to the intermediate implant being in a position relative to the tibial implant such that said intermediate implant is substantially centered relative to the point of origin ($P_o$) about which the movements of the tibia relative to the talus in anteroposterior translation, in mediolateral translation, and in rotation about the medullary axis (ZZ) of the tibia take place.

4. The ankle prosthesis component according to claim 3, wherein the intermediate implant is oriented relative to the tibial implant and the talar implant such that the movement axes of the prosthesis substantially coincide with the natural anatomical axes of the ankle of the patient.

5. The ankle prosthesis component according to claim 3, wherein the curved surface comprises a frustoconical shape.

6. The ankle prosthesis component according to claim 1, wherein the intermediate implant is configured to couple with a fastener that is configured to couple with the tibia implant thereby locking the angle of the intermediate implant relative to the tibia implant.

7. The ankle prosthesis component according to claim 1, wherein the angle is the angle at which stresses exerted on the intermediate implant are less than at other angles.

8. An ankle prosthesis comprising:
a) a talar implant;
b) a tibial implant; and
c) an intermediate implant configured to be interposed between the tibial implant and the talar implant, the intermediate implant comprising a top portion and a bottom portion, the bottom portion defining a curved surface configured to move relative to the talar implant at a contact interface and the top portion being configured to couple to the tibia implant such that the intermediate implant can rotate relative to the tibia about a medullary axis (ZZ') of the tibia so as to position the intermediate implant in a rotational position relative to the tibia implant and can lock relative to the tibia implant thereby impeding rotation relative to the tibia implant once positioned, and such that the intermediate implant can move linearly along an axis which is substantially normal to said medullary axis and can lock relative to the tibia thereby impeding linear movement along the axis once positioned.

9. The ankle prosthesis according to claim 8, further comprises a fastener configured to couple with the tibia implant thereby locking the rotational position of the intermediate implant relative to the tibia implant.

10. The ankle prosthesis component according to claim 8, wherein the curved surface is configured such that the contact interface comprises a frustoconical shape.

11. An ankle prosthesis component for use with an ankle, comprising an intermediate implant configured to be disposed between a tibia implant and a talar implant, the intermediate implant comprising a top portion and a bottom portion, the bottom portion defining a curved surface configured to move relative to the talar implant at a contact interface and the top portion being configured to couple to the tibia implant such that the intermediate implant can rotate relative to the tibia about a first axis so as to position the intermediate implant at an angle relative to the tibia implant and can lock relative to the tibia implant thereby impeding rotation relative to the tibia implant once positioned, wherein the curved surface is configured such that the contact interface comprises a frustoconical shape.

12. An ankle prosthesis component for use with an ankle, comprising:
   a) a talar implant configured to couple to couple to a tibia;
   b) a tibial implant configured to couple to a talus; and
   and an intermediate implant configured to be disposed between the tibia implant and the talar implant, the intermediate implant comprising a top portion and a bottom portion, the bottom portion defining a curved surface configured to move relative to the talar implant at a contact interface and the top portion being configured to couple to the tibia implant such that the intermediate implant can rotate relative to the tibia about a first axis so as to position the intermediate implant at an angle relative to the tibia implant and can lock relative to the tibia implant thereby impeding rotation relative to the tibia implant once positioned and such that the intermediate implant can move linearly along a second axis which is substantially normal to the first axis and can lock relative to the tibia thereby impeding linear movement along the second axis once positioned.

* * * * *